United States Patent [19]

Mehallick

[11] 3,955,283
[45] May 11, 1976

[54] FLEXIBLE HANDPIECE MOUNTED CONTROL FOR DENTAL DRILLS

[76] Inventor: Timothy William Mehallick, P.O. Box 12, Scottdale, Pa. 15683

[22] Filed: Oct. 31, 1974

[21] Appl. No.: 519,746

[52] U.S. Cl. .......................................... 32/26; 32/28
[51] Int. Cl.² ........................................... A61C 19/02
[58] Field of Search ............. 32/26, 27, 28, DIG. 1, 32/DIG. 3; 415/123, 151, 156, 503, 29

[56] References Cited
UNITED STATES PATENTS

| | | | |
|---|---|---|---|
| 1,556,181 | 10/1925 | Tyree | 32/28 |
| 2,776,488 | 1/1957 | Brown | 32/28 |
| 3,052,984 | 9/1962 | Mitthauer et al. | 32/27 |
| 3,129,511 | 4/1964 | Williams | 32/28 |
| 3,244,846 | 4/1966 | Kopp | 32/27 |
| 3,256,603 | 6/1966 | White | 32/27 |
| 3,346,958 | 10/1967 | Sinatra et al. | 32/28 |
| 3,423,068 | 1/1969 | Hall | 32/27 X |
| 3,449,831 | 6/1969 | Vandis | 32/26 |
| 3,567,330 | 3/1971 | Apelskog et al. | 32/27 X |
| 3,568,318 | 3/1971 | Martin | 32/27 |

*Primary Examiner*—Louis G. Mancene
*Assistant Examiner*—Jack Q. Lever
*Attorney, Agent, or Firm*—Jon M. Lewis

[57] ABSTRACT

This invention discloses a flexible handpiece mounted control for dental drills. Two embodiments are disclosed whereby the control can be mounted externally on a standard handpiece or part of a specially designed handpiece. Both embodiments provide a tube that is designed to permit the uninterrupted flow of fluid. When an external load (finger pressure) is applied to the tube, an obstruction to the fluid flow occurs. This obstruction to the fluid flow is a back pressure that may be monitored and used to control dental drill speed and/or water flow to the drill.

7 Claims, 8 Drawing Figures

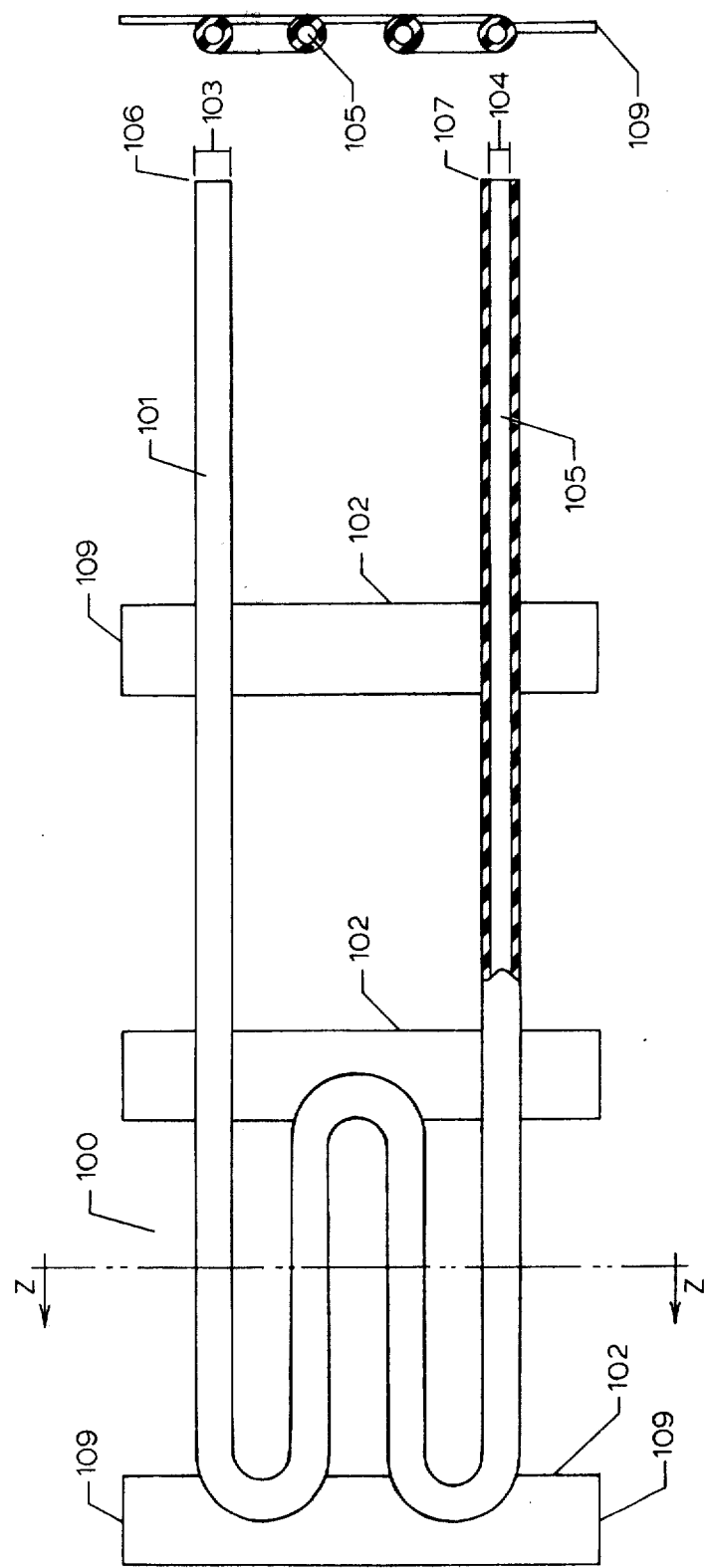

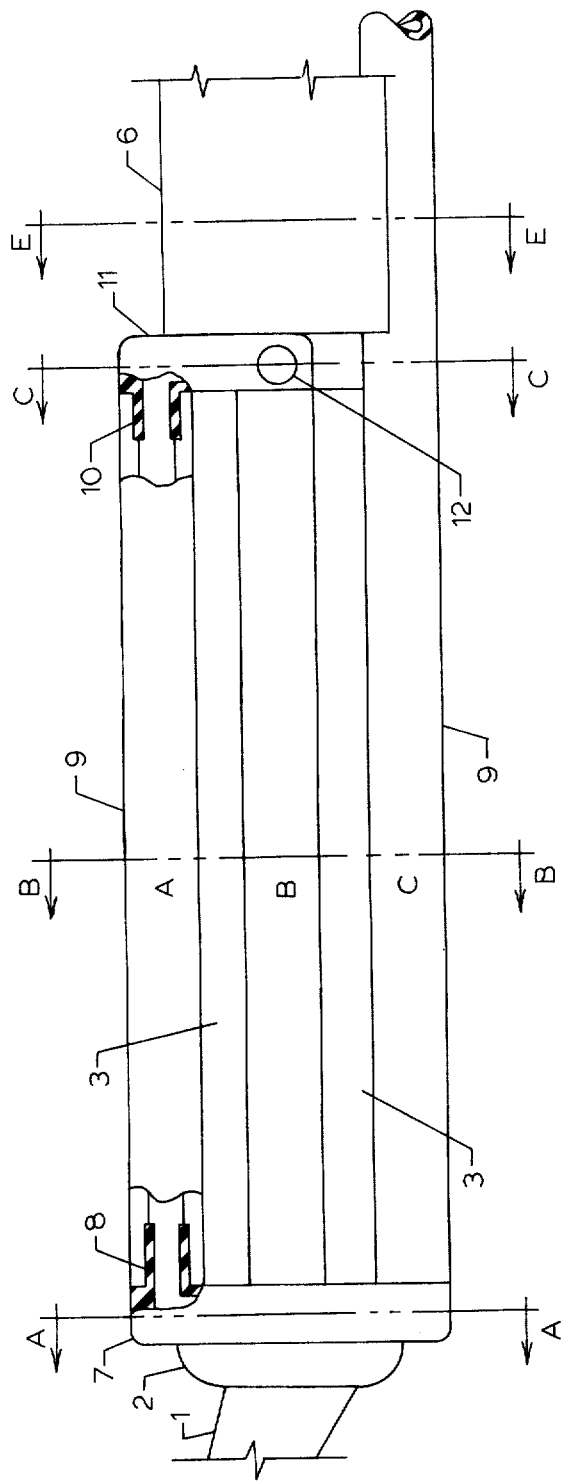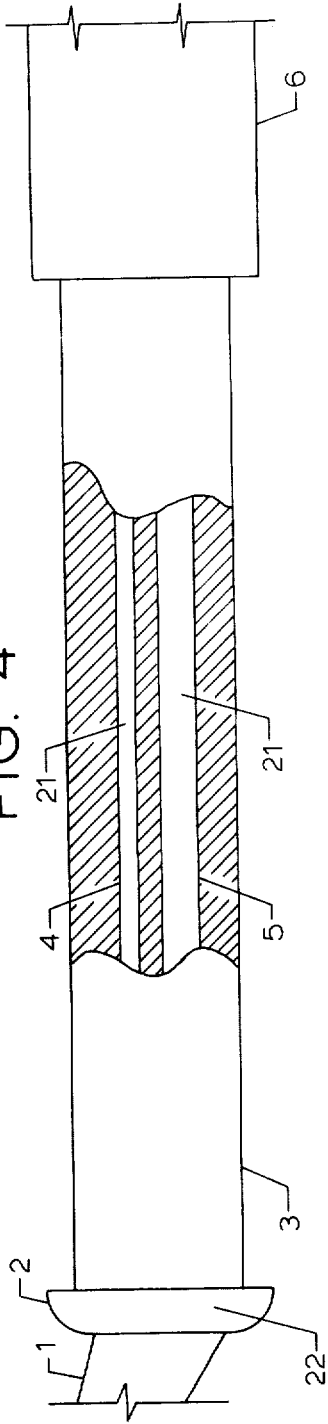

FLEXIBLE HANDPIECE MOUNTED CONTROL FOR DENTAL DRILLS

BACKGROUND OF INVENTION

1. Field Of Invention

This invention discloses a novel flexible handpiece mounted control for dental drills. The invention can be used to vary the drill speed and/or water flow of fluid drive hand operated dental drills.

Presently, fluid driven dental drills are widely used by dentists. The fluid drive drill runs at relatively high speed with the resultant shorter drilling time. Thus, a dentist can effectively cut, grind and smooth with more control of quality at a faster rate than non-fluid drive drills. In Additon, the faster rate provides for better patient acceptance.

2. Description Of Prior Art

A variety of control means are known in the art. The most widely used control apparatus is a foot operated controller. Foot operated controllers can provide for a proper drill speed control but physically limit a dentist's movement since the dentist must stay close to the control. This presents a fatigue problem as the dentist must remain in one basic position. The foot operated control does not have the coordination advantages of hand controls since dental operators require hand, eye and foot coordination instead of just hand and eye coordination.

Various hand piece mounted mechanical or pneumatic controls are known in the art. The mechanical handpiece mounted controls generally use lever action. For example, in Pat. No. 3,128,079 an outwardly pivoting control lever is mounted on the drill handpiece. This lever permits the application of a hand squeezing manner in controlling drill speed. There is a great tendancy on the part of the pivotal lever controls previously known in the art to bring about a jerking movement on the grasped handpiece, with the resultant lessening of control by a dentist. Prolonged use of the lever operated drill tends to cause fatigue due to the jerking movement and the set location of the lever. Since the lever is placed in a set location on the handpiece, the dentist would have to hold the handpiece in such a manner as to effectively operate the lever. When the lever is in a set position, the handpiece has to be held in a set position and fatigue sets in after prolonged use. Further, the dentist's access to the teeth is somewhat limited due to the nature of lever design and a patient's mouth.

In U.S. Pat. No. 3,423,068 a slidible fingertip control is disclosed to operate pneumatic surgical instruments. An actuator slides along the drill housing to control drill speed. The use of the slidible fingertip control would present some fatigue problems to the dentist due to the set location of the slide. If the slide could only be used one way, the dentist would have to hold the handpiece that way as long as he used the drill. An Additional problem is that the tip control does not provide for control of water flow at the head of the handpiece. Further, the tip actuator presents some access problems to certain areas of the mouth due to the nature of the actuator location and location of teeth in the patient's mouth. An additional problem with all mechanical controls is that they are subject to wear with the resultant expensive maintenance and replacement problems. The nature of all present mechanical controls providing a set location presents fatigue problems because the dentist is required to hold the handpiece in a certain way to control the drill during his daily operations over a prolonged period of time.

The pneumatically operated handpiece mounted control fluid drive drill has the advantage of being handpiece mounted, simple to operate, not required to be placed in a set constant position on handpiece and does not hinder drill access to a patient's mouth. An example of a pneumatic control is U.S. Pat. No. 3,568,318. A pneumatic control is disclosed along with various regulators for controlling the fluid driven handpiece, water flow at the head of the handpiece as well as the direct control of vacuum aspiration. The control can be placed at any location on the handpiece desired by the dentist. Of course, the handpiece would have to be designed to permit the placement of the control. Once that location was determined, the location would then be constant on that handpiece. The pneumatic control is simple to operate since finger pressure over the exhaust nozzle is all that would be required to control speed. Due to the nature of the dentist's work, the finger would tend to get wet and some slippage of the finger may occur over the exhaust nozzle. The result would be less control over drill speed. The exhaust nozzle placement on the handpiece itself results in air exhausting and close proximity to the patient, the dentist and the work area.

Of course, to control various speeds through the use of the exhaust nozzle would be difficult in that the dentist is required to provide a set back pressure for the desired speed. In order to vary the speed, the dentist would have to raise or lower his finger over the exhaust nozzle. Every movement including the movement of air from the nozzle itself would tend to change the speed. Thus, except for full speed, the exhaust would be too delicate to control various intermediate speeds between stop and full speed.

The present invention overcomes the disadvantages of the prior art by providing a flexible handpiece mounted control for fluid driven dental drills. The present invention eliminates disadvantages of the prior art pneumatic controls; namely, the exhaust of air at the location of the work area, the control piece at only one set location, the slippage and resultant lessening of control that may occur due to the nature of the dentist's work and the design of the exhaust nozzle and the difficulty to control various speeds other than full speed at the exhaust nozzle.

The disadvantages of the mechanically operated handpiece mounted controls are not present in this invention; e.g. the fatigue problems arising due to the set location of the mechanical lever, the relatively expensive maintenance and replacement problems that arise with mechanical elements in constant use where accuracy is required, and the hinderance of access to various locations in a patient's mouth. The problems associated with the foot controllers, such as the limits on a dentist's physical location, fatigue problems, additional coordination required between the eye, hand and foot instead of just the eye and hand are not present in this invention.

This invention contemplates a simply operated pneumatic control with a relatively high degree of drill speed control as well as water flow control. The invention discloses a tube of sufficient flexibility that it permits a dentist to apply obstruction to air flowing through the tube by placing finger or hand pressure on the tube. The drill speed can be controlled by placing an external load at any point on the flexible tube of the invention, thus lessening a dentist's hand fatigue since he can apply pressure accordign to his desires at the location of his desires. The invention requires a minimal maintenance and is easily and economically replaceable when subject to abuse or wear. Exhaust air from the flexible tube is focused in any area desired away from the work area.

SUMMARY OF INVENTION

This invention consists of two embodiments, although it should be appreciated that other embodiments illustrating the nature and principle of this invention are practical. The present invention relates to a pneumatically operated flexible handpiece mounted control for dental drills. A flexible tube can be placed external to an existing handpiece for one embodiment or placed on a properly designed handpiece for another embodiment. The flexible tube is designed to permit the uninterrupted flow of control fluid at constant pressure, preferably air. The tube is placed so that the dentist can apply pressure on the tube to cause an obstruction to the fluid flow in the tube. This obstruction, or back pressure, can be used to vary the drill speed and/or water flow by the use of any generally known regulating means or combinations thereof. The external load placed upon the flexible tube may be variable depending upon that speed desired by the dentist. It is important to this invention that a tube be of sufficient flexibility that the dentist can restrict the flow of air passing through the tube by finger or hand pressure.

A great range of speeds and/or water flow is available to the dentist depending upon his needs and desires. Due to the nature of the tube, the dentist can have a high range of control; i.e. small pressure low speed, greater speed, complete obstruction, top speed. Speed range of the drill is subject only to the type of regulating means used. By the use of proper regulating means, the various amounts of obstruction placed on the tubing can provide a water flow at the drill head as well as the controlled drill speed. The water flow can be set to be either infinitely variable in amount depending upon the desires of the dentist or designed to start at a set drill speed.

The embodiment designed to be placed externally on a standard handpiece can be connected to the handpiece by placing the tube on tabs in such a manner that the tabs overlap the tube in order to have tab ends. Any standard glue or epoxy would be applied to the tab ends. By wrapping the tube with the tabs around a standard handpiece tightly, then overlapping the tab ends, a tight fit is achieved. Once the embodiment is placed on the handpiece, it is ready for use.

One end of the tube would be adapted to be connected to an input to act as an air source and the other would act as an exhaust. Preferably, the tube is placed on the tabs in such a manner that it is directed from one of the tabs to the furthermost tab in a straight line; then bent away from such tab and directed in a parallel line towards the first tab; then bent back again towards the furthermost tab and directed in parallel; and finally, bent away from the furthermost tab towards the first tab and directed in parallel. When the preferred embodiment is placed on the handpiece, the resultant design is thus arranged in a triple loop configuration with the tube passages relatively parallel to the handpiece. This design is important as it permits the dentist to apply pressure on the tube to create obstruction at numerous locations on the triple loops. Thus, an advantage of the triple loop design is many variable locations for applying pressure in control with minimal tendency to hinder dental operations or access to a patient's mouth.

The embodiment designed for placement of the tube within a specially designed handpiece preferably has the tube placed in parallel, surrounding a central body. This tube is designed to permit the flow of air in one direction only. The tube would be connected to interconnectors so as to permit air to flow from one tube toward the interconnector, then the air flow would pass into the interconnector, through the interconnector and out the tube in sequence until exhausted. Preferably, more than one tube is present and the dentist would be able to apply finger pressure to cause obstruction at any place along the tube.

The tube can be made of any substance that permits the unobstructed flow of air and subject to the application of force to cause obstruction to the flow. Preferably, the tube is made of an ethylene proplyene diene monomer or the like with an inside diameter of 0.08 ± 0.015 in. and an outside diameter of 0.16 ± 0.02 in. Further, the tube is designed so that a two ounce pressure will present the first noticeable obstruction for control purposes. A four ounce pressure would cause complete obstruction to the tube. For cleanliness and sterility purposes, both embodiments are autoclavable and disinfectible with normal disinfectants used by dentists. In addition, both embodiments are designed for simple and economical replacement of the tube if it should be subject to abuse and wear. Any constant air pressure through the tube would be adequate. The preferable range for operation would be a set pressure of between 2 ½ p.s.i. and 8 ½ p.s.i.

The attached drawings show, for purpose of exemplification without limiting the present invention and claims thereto, two practical embodiments illustrating the principals of this invention and its application.

DESCRIPTION OF THE DRAWING

FIG. 1 is a partially cut-away horizontal view of the first embodiment of the present invention.

FIG. 2 is a sectional view of the first embodiment of the present invention taken along line $z-z$ of FIG. 1.

FIG. 3 is a partially cut-away horizontal view of the second embodiment of the present invention.

FIG. 4 is a partially cut-away sectional horizontal view of the second embodiment of the present invention.

DESCRIPTION OF THE PREFERRED EMBODIMENTS

Figure 5:
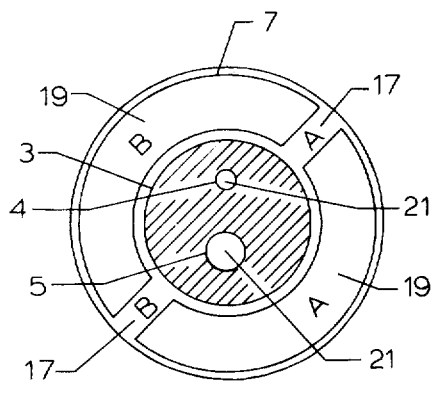
FIG. 5 is a sectional view of the second embodiment of the present invention taken along the line $a-a$ of FIG. 3.

Referring to the drawings, FIG. 1 portrays the flexible handpiece mounted control for dental drills 100. Tube 101 is designed to be adapted to any handpiece of a dental drill (not shown) and is dimensioned to permit the passage of a gaseous control fluid. The tube 101 is adapted to be connected to a source (not shown) to provide control fluid that enters the tube at the input 106. The control fluid, preferably air, then travels through the tube 101 and leaves the tube 101 at the exhaust outlet 107 to be exhausted. The tube 101 is attached to tabs 102 in order to fix the location of the tube 101 and to facilitate the connection of the flexible handpiece mounted control 100 on any existing fluid driven dentist drill handpiece (not shown).

In the preferred embodiment the tube is designed in such a manner that the input 106 would be directed from one of the tabs 102 to the furthermost tab 102 in a straight line; then bent away from such tab and directed in a parallel line towards the first tab; then bent back again towards the furthermost tab and directed in parallel; and then, bent away from the furthermost tab to the first tab and directed parallel to the exhaust outlet 107. The resultant design is thus arranged in a triple loop configuration with the tube passages relatively parallel. The flexible handpiece mounted control 100 can be wrapped around any standard handpiece and attached by placing any connection means (not shown), preferably glue or epoxy, on tab ends 109. The connection means would be placed on one tab end 109 and the opposite tab end 109 would be placed on top of the connection means in order to hold the tab 102 with tube 101 tightly around the handpiece.

Referring to FIG. 2, tube 101 has an outside diameter 103, inside diameter 104 and a resultant annular space 105. The control fluid (preferably air) passes through the annular space 105. As an external force, e.g. finger pressure, is placed upon the tube 101, the inside diameter 104 collapses causing the annular space 105 to constrict. This constriction of the annual space 105 causes an obstruction in the passage of control fluid. It is important to the present invention that the tube is sufficiently flexible to allow constriction by application of finger pressure or hand pressure. By means not shown nor claimed, this obstruction to the control fluid is monitored and used to regulate drill speed and/or water flow in a standard pneumatic dental drill. Any presently available regulators or combinations of regulator parts may be used to monitor the control fluid flow and correspondingly control drill speed and water flow.

The tube 101 preferably has an outside diameter of $0.16 \pm 0.02$ in. The inside diameter is preferably $0.08 \pm 0.015$ in. The tube 101 is preferably made of ethylene proplyene diene monomer or the like which has the ability to have a first noticeable constriction on the inside diameter when an external load pressure of 2 ounces is applied. A 4 ounce pressure would cause a complete obstruction. This flexible material has good wear characteristics, is relatively inexpensive in cost, has a good ability to produce a tube of desired dimensions, and is autoclavable and disinfectable in the normal solutions that dentists use without causing undue harm to the control characteristics of the tube. Preferably, the invention operates at a constant air pressure set between 2 ½ p.s.i. and 8 ½ p.s.i.

It is preferred that the tube 101 is dimensioned in a triple loop configuration with tube passages relatively parallel. The input 106 and exhaust outlet 107 are parallel. This configuration provides for a maximum amount of area available to the dentist to apply an external load such as finger pressure without hindering the drill operation.

FIG. 3 and FIG. 4 of the drawing show the second embodiment of the invention where drill body 22 is preferably cast with two internal annular spaces 21. One of the internal annular spaces 21 acts as a water supply line 4 and the other acts as air supply line 4. In practice, water flows through the water supply line 4 to the drill head and then out into the area directed by the dentist (not shown). Air flows through the air supply line 5 to actuate and run the fluid driven dental drill (not shown). The drill body 22 is preferably constructed in one piece with the following configurations: a drill offset 1 to hold the drill (not shown), a front retainer 2, a handpiece body 3 and back member 6. Tube 9 is connected to front element interconnector 7 and rear element interconnector 11. The front element interconnector 7 is designed to fit over the handpiece body 3 and fit next to the front retainer 2. Rear element interconnector 11 is designed to fit on the back member 6. The tube 9 is preferably manufactured out of a material with similar characteristics and of similar dimensions to those of the first embodiment.

Figure 8:
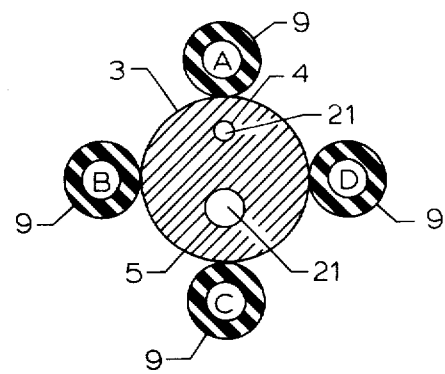
FIG. 8 is a sectional view of the second embodiment of the present invention taken along line $b-b$ of FIG. 3.

The placement of the tube 9 is further portrayed in FIG. 8. Handpiece body 3 is one piece construction with two internal annular space 21 comprising water supply line 4 and air supply line 5. Tube 9 is place around and next to the hand piece body 3. Of course, it should be pointed out that as many or as few tubes can be placed at any location around the handpiece body as desired. In this embodiment we noted the letters A, B, C and D on four sections of the tube 9 for purposes of description of fluid flow.

Referring to FIG. 3 and FIG. 5, front interconnector 7 contains front interconnector portlet 8. The front element interconnector 7 is designed so that a portion of the tube 9 connects to the front interconnector portlet 8. Front element interconnector 7 is internally dimensioned with front chambers 19. Front interconnector dividers 17A and 17B separate the front chambers 19A and 19B. The front chambers 19 are designed to receive air from one portion of the tube 9 and pass it back into another portion of the tube 9. For descriptive purposes, we show four portions of the tube: 9A, 9B, 9C and 9D.

Figure 6:
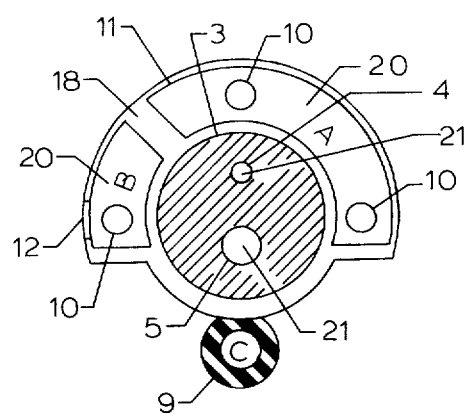
FIG. 6 is a sectional view of the second embodiment of the present invention taken along line $c-c$ of FIG. 3.

Referring to FIG. 6 and FIG. 3, rear element interconnector 11 contains rear interconnector portlet 10. The rear interconnector portlet is designed so that portions of the tube 9 connect to the rear interconnector portlet 10. Rear element interconnector 11 is designed with rear chambers 20. Rear interconnector divider 18 separates the rear chambers 20A and 20B. The rear element interconnector 11 and rear chambers 20 are dimensioned to receive air from one portion of the tube 9 and pass it out into either another portion of the tube 9 or exhaust portlet 12.

Referring to FIGS. 3, 5, 6 and 8, air flows through tube 9C into the front element interconnector 7 and enters front chamber 19A. The air then flows through front chamber 19A out through tube 9D, as shown in FIG. 8. Referring to FIGS. 3, 6, and 8, air would pass through tube 9D into rear element interconnector 11, then through rear chambers 20A and out into tube 9A.

Referring now to FIGS. 3, 5 and 8, air would then pass through tube 9A into front chamber 19B and back out into tube 9B.

Referring to FIGS. 3, 5 and 8 again, air finally passes through tube 9B into rear element interconnector 11, through rear chamber 20B and out into the atmosphere by way of exhaust portlet 12.

Figure 7:
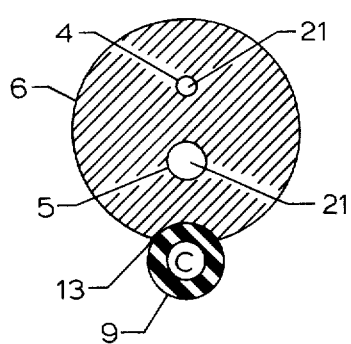
FIG. 7 is a partial sectional view of the second embodiment of the present invention taken along line $e-e$ of FIG. 3.

Referring to FIG. 6 and 7, back member 6 is preferably solidly cast with two internal annular spaces 21. The internal annular spaces 21 act as water supply line 4 and air supply line 5. A concave support guide 13 is dimensioned with back member 6 to provide support and protection for tube 9C. Tube 9C is adapted to be connected to an air supply source.

Having described my invention, I claim:

1. A fluid driven dental drill with pneumatically operated handpiece control comprising:
   a. a drill body dimensioned with internal annular spaces for a water supply line and an air supply line; and
   b. a tube attached externally to the drill body, designed to permit the passage of air and of sufficient flexibility that a pressure of 2.0 ± 0.5 ounces to the outside diameter causes a first noticeable obstruction to the passage of air through the tube and a 4.0 ± 0.5 ounce pressure causes complete obstruction to the passage of air through the tube, adapted to be connected to an air supply source on the one hand and an exhaust on the other.

2. A fluid driven dental drill of claim 1 wherein the tube comprises:
   an ethylene propylene diene monomer with an inside diameter of 0.08 ± 0.015 in. with an outside diameter of 0.16 ± 0.02 in.

3. The fluid driven dental drill of claim 1 wherein said drill body comprises:
   a. a drill off-set dimensioned to hold a drill;
   b. a front retainer connected to the drill off-set and dimensioned to anchor the tube;
   c. a handpiece body, connected to the front retainer;
   d. a back member connected to the handpiece body and dimensioned to provide support for the tube;
   e. a front element interconnector, dimensioned with an internal front chambers and a front interconnector portlet that provides for connection with the tube; and
   f. a rear element interconnector, dimensioned with internal rear chambers, an exhaust portlet, and rear interconnector portlets that provide for connections with the tube and the exhaust portlet.

4. A pneumatically operated flexible handpiece mounted control for fluid driven dental drills comprising:
   a. a tube designed to permit the passage of air, and of sufficient flexibility that a pressure of 2.0 ± 0.5 ounces to the outside diameter causes a first noticeable obstruction to passage of air through the tube and a 4.0 ± 0.5 ounce pressure causes complete obstruction to passage of air through the tube, mounted on any handpiece of a standard fluid driven dental drill and adapted to be connected to an air supply source on the one hand and an exhaust on the other.

5. The pneumatically operated flexible handpiece mounted control for fluid driven dental drills of claim 1 further comprising:
   a. tabs dimensioned to be attached to the tube and designed so that the ends of each tab would overlap when fit on any handpiece of an existing fluid driven dental drill; and
   b. connection means for holding the ends of a tab together.

6. The pneumatically operated flexible handpiece mounted control for fluid driven dental drills of claim 1 wherein the tube comprises:
   an ethylene propyene diene monomer with an inside diamter of 0.08 ± 0.015 in. and an outside diameter of 0.16 ± 0.02 in.

7. The pneumatically operated flexible handpiece mounted control for fluid driven dental drills of claim 5, wherein the tube is placed on the tab in such a manner that it is directed from one of the tabs to the furthermost tab in a straight line; then bent away from such tab and directed in a parallel line towards the first tab; then bent back again towards the furthermost tab and directed in parallel; and finally, bent away from the furthermost tab towards the first tab and directed in parallel.

* * * * *